United States Patent [19]
Gasser et al.

[11] Patent Number: 5,859,337
[45] Date of Patent: Jan. 12, 1999

[54] GENES CONFERRING SALT TOLERANCE AND THEIR USES

[75] Inventors: Charles S. Gasser, Davis, Calif.; Veronica Lippuner, Zurich, Switzerland

[73] Assignee: The Regents of the University of California, Oakland, Calif.

[21] Appl. No.: 471,717

[22] Filed: Jun. 6, 1995

[51] Int. Cl.[6] .............................. A01H 5/00; C12N 15/82
[52] U.S. Cl. .................. 800/205; 536/23.1; 536/23.6; 435/69.1; 435/172.3; 435/320.1; 435/419
[58] Field of Search .......................... 800/205; 536/23.1, 536/23.6; 435/69.1, 172.3, 240.4, 320.1, 419

[56] References Cited

PUBLICATIONS

Cyert, Martha S., et al. (1991) "Yeast has homologs (CNA1 and CNA2 gene products) of mammalian calcineurin, a calmodulin-regulated phosphoprotein phosphatase", *Proc. Natl. Acad. Sci. USA*, 88:7376–7380.

Dix, Philip J. (1993) "The role of mutant cell lines in studies on environmental stress tolerance: an assessment", *The Plant Journal*, 3(2):309–313.

Murguia, Jose Ramon, et al. (1995) "A Salt–Sensitive 3' (2'), 5'–Bisphosphate Nucleotidase Involved in Sulfate Activation", *Science*, 267:232–234.

Tarczynski, Mitchell C., et al. (1993) "Stress Protection of Transgenic Tobacco by Production of the Osmolyte Mannitol", *Science*, 259:508–510.

Takatsuji, Hiroshi, et al. (1994) "A New Family of Zinc Finger Proteins in Pentunia: Structure, DNA Sequence Recognition, and Floral Organ–Specific Expression", *The Plant Cell*, 6:947–958.

Finnegan et al. (1994) Bio/Technology 12: 883–888.
Malathi et al. (1994) J. Biol Chem 269 (37) : 22945–22951.

*Primary Examiner*—Elizabeth F. McElwain
*Attorney, Agent, or Firm*—Townsend and Townsend and Crew LLP

[57] ABSTRACT

The present invention provide nucleic acids encoding polypeptides which confer salt tolerance and plants an other organisms. The nucleic acids can be used to produce transgenic cultivars suitable for growth under saline conditions.

13 Claims, 2 Drawing Sheets

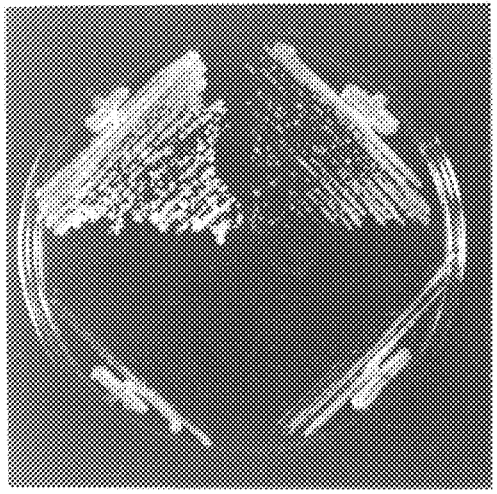
Figure 2A
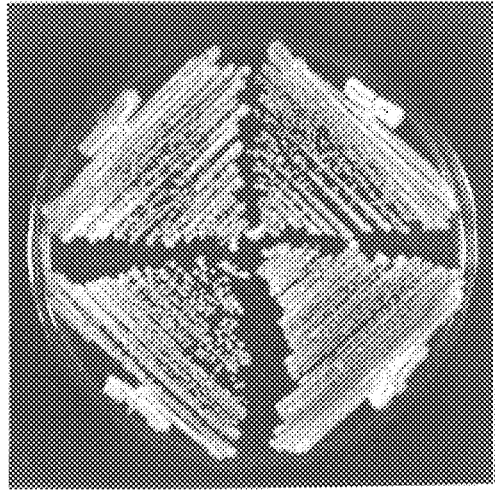
Figure 2B
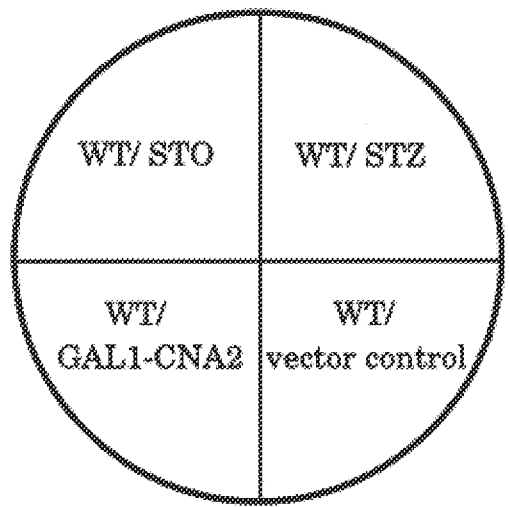

5,859,337

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 940 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 55..738

( x i ) SEQUENCE DESCRIPTION: SEQ ID NO:1:

```
GCAACCTTCA  AACTAAAACT  CGAGAGACAA  GAAATCCTCA  GAATCTTTAA  CTTA ATG                 57
                                                                 Met
                                                                 1

GCG  CTC  GAG  GCT  CTT  ACA  TCA  CCA  AGA  TTA  GCT  TCT  CCG  ATT  CCT  CCT      105
Ala  Leu  Glu  Ala  Leu  Thr  Ser  Pro  Arg  Leu  Ala  Ser  Pro  Ile  Pro  Pro
               5                    10                        15

TTG  TTC  GAA  GAT  TCT  TCA  GTC  TTC  CAT  GGA  GTC  GAG  CAC  TGG  ACA  AAG      153
Leu  Phe  Glu  Asp  Ser  Ser  Val  Phe  His  Gly  Val  Glu  His  Trp  Thr  Lys
          20                         25                        30

GGT  AAG  CGA  TCT  AAG  AGA  TCA  AGA  TCC  GAT  TTC  CAC  CAC  CAA  AAC  CTC      201
Gly  Lys  Arg  Ser  Lys  Arg  Ser  Arg  Ser  Asp  Phe  His  His  Gln  Asn  Leu
               35                        40                   45

ACT  GAG  GAA  GAG  TAT  CTA  GCT  TTT  TGC  CTC  ATG  CTT  CTC  GCT  CGC  GAC      249
Thr  Glu  Glu  Glu  Tyr  Leu  Ala  Phe  Cys  Leu  Met  Leu  Leu  Ala  Arg  Asp
50                       55                        60                        65

AAC  CGT  CAG  CCT  CCT  CCT  CCT  CCG  GCG  GTG  GAG  AAG  TTG  AGC  TAC  AAG      297
Asn  Arg  Gln  Pro  Pro  Pro  Pro  Pro  Ala  Val  Glu  Lys  Leu  Ser  Tyr  Lys
                    70                        75                        80

TGT  AGC  GTC  TGC  GAC  AAG  ACG  TTC  TCT  TCT  TAC  CAA  GCT  CTC  GGT  GGT      345
Cys  Ser  Val  Cys  Asp  Lys  Thr  Phe  Ser  Ser  Tyr  Gln  Ala  Leu  Gly  Gly
               85                        90                        95

CAC  AAG  GCA  AGC  CAC  CGT  AAG  AAC  TTA  TCA  CAG  ACT  CTC  TCC  GGC  GGA      393
His  Lys  Ala  Ser  His  Arg  Lys  Asn  Leu  Ser  Gln  Thr  Leu  Ser  Gly  Gly
          100                        105                       110

GGA  GAT  GAT  CAT  TCA  ACC  TCG  TCG  GCG  ACA  ACC  ACA  TCC  GCC  GTG  ACT      441
Gly  Asp  Asp  His  Ser  Thr  Ser  Ser  Ala  Thr  Thr  Thr  Ser  Ala  Val  Thr
          115                        120                       125

ACT  GGA  AGT  GGG  AAA  TCA  CAC  GTT  TGC  ACC  ATC  TGT  AAC  AAG  TCT  TTT      489
Thr  Gly  Ser  Gly  Lys  Ser  His  Val  Cys  Thr  Ile  Cys  Asn  Lys  Ser  Phe
130                      135                       140                       145

CCT  TCC  GGT  CAA  GCT  CTC  GGC  GGA  CAC  AAG  CGG  TGC  CAC  TAC  GAA  GGA      537
Pro  Ser  Gly  Gln  Ala  Leu  Gly  Gly  His  Lys  Arg  Cys  His  Tyr  Glu  Gly
                    150                       155                       160

AAC  AAC  AAC  ATC  AAC  ACT  AGT  AGC  GTG  TCC  AAC  TCC  GAA  GGT  GCG  GGG      585
Asn  Asn  Asn  Ile  Asn  Thr  Ser  Ser  Val  Ser  Asn  Ser  Glu  Gly  Ala  Gly
               165                       170                       175

TCC  ACT  AGC  CAC  GTT  AGC  AGT  AGC  CAC  CGT  GGG  TTT  GAC  CTC  AAC  ATC      633
Ser  Thr  Ser  His  Val  Ser  Ser  Ser  His  Arg  Gly  Phe  Asp  Leu  Asn  Ile
          180                       185                       190

CCT  CCG  ATC  CCT  GAA  TTC  TCG  ATG  GTC  AAC  GGA  GAC  GAC  GAA  GTC  ATG      681
Pro  Pro  Ile  Pro  Glu  Phe  Ser  Met  Val  Asn  Gly  Asp  Asp  Glu  Val  Met
     195                       200                       205

AGC  CCT  ATG  CCG  GCG  AAG  AAG  CCT  CGG  TTT  GAC  TTT  CCG  GTC  AAA  CTT      729
Ser  Pro  Met  Pro  Ala  Lys  Lys  Pro  Arg  Phe  Asp  Phe  Pro  Val  Lys  Leu
210                      215                       220                       225

CAA  CTT  TAA  GGAAATTTAC  TTAGACGATA  AGATTTCGTT  TGTATACTGT                       778
Gln  Leu  *
```

```
TGAGAGTTGT GTAGGAATTT GTTGACTGTA CATACCAAAT TGGACTTTGA CTGATTCCAA       838

TTCTTCTTGT TCTTTCATTT TAAAAATTAT TAAACCGATT CTTTACCACA AAAAAAAAA       898

AAAAAAAAAA AAAAAAAAA AAAAAAAAAA AAAAAAAAA AA                          940
```

( 2 ) INFORMATION FOR SEQ ID NO:2:

( i ) SEQUENCE CHARACTERISTICS:
  ( A ) LENGTH: 227 amino acids
  ( B ) TYPE: amino acid
  ( D ) TOPOLOGY: linear ( i i ) MOLECULE TYPE: protein ( x i ) SEQUENCE DESCRIPTION: SEQ ID NO:2:

```
Met Ala Leu Glu Ala Leu Thr Ser Pro Arg Leu Ala Ser Pro Ile Pro
 1               5                  10                  15

Pro Leu Phe Glu Asp Ser Ser Val Phe His Gly Val Glu His Trp Thr
             20                  25                  30

Lys Gly Lys Arg Ser Lys Arg Ser Arg Ser Asp Phe His His Gln Asn
             35                  40                  45

Leu Thr Glu Glu Glu Tyr Leu Ala Phe Cys Leu Met Leu Leu Ala Arg
     50                  55                  60

Asp Asn Arg Gln Pro Pro Pro Pro Ala Val Glu Lys Leu Ser Tyr
 65              70                  75                      80

Lys Cys Ser Val Cys Asp Lys Thr Phe Ser Ser Tyr Gln Ala Leu Gly
                 85                  90                  95

Gly His Lys Ala Ser His Arg Lys Asn Leu Ser Gln Thr Leu Ser Gly
                 100                 105                 110

Gly Gly Asp Asp His Ser Thr Ser Ser Ala Thr Thr Thr Ser Ala Val
             115                 120                 125

Thr Thr Gly Ser Gly Lys Ser His Val Cys Thr Ile Cys Asn Lys Ser
     130                 135                 140

Phe Pro Ser Gly Gln Ala Leu Gly Gly His Lys Arg Cys His Tyr Glu
145                 150                 155                 160

Gly Asn Asn Asn Ile Asn Thr Ser Ser Val Ser Asn Ser Glu Gly Ala
                 165                 170                 175

Gly Ser Thr Ser His Val Ser Ser Ser His Arg Gly Phe Asp Leu Asn
             180                 185                 190

Ile Pro Pro Ile Pro Glu Phe Ser Met Val Asn Gly Asp Asp Glu Val
             195                 200                 205

Met Ser Pro Met Pro Ala Lys Lys Pro Arg Phe Asp Phe Pro Val Lys
     210                 215                 220

Leu Gln Leu
225
```

( 2 ) INFORMATION FOR SEQ ID NO:3:

( i ) SEQUENCE CHARACTERISTICS:
  ( A ) LENGTH: 1033 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i x ) FEATURE:
  ( A ) NAME/KEY: CDS
  ( B ) LOCATION: 122..868

( x i ) SEQUENCE DESCRIPTION: SEQ ID NO:3:

```
TCTGAACCTA CGCTTCTGCT AAGCTATTCT AAGAGAAGCC AGACTAGCAA TAAACCCTTC        60

ATTTTAAGCA TTCTGTTTCC TTCTTGAGAA ACCTAGATAT TTTGGTTTCT TGTATCCGGT       120

G ATG AAG ATA CAG TGT GAT GTG TGT GAG AAA GCT CCG GCG ACG GTG           166
  Met Lys Ile Gln Cys Asp Val Cys Glu Lys Ala Pro Ala Thr Val
      230               235                   240

ATT TGT TGC GCC GAC GAA GCT GCT CTC TGT CCT CAA TGC GAC ATC GAG         214
Ile Cys Cys Ala Asp Glu Ala Ala Leu Cys Pro Gln Cys Asp Ile Glu
    245             250                 255

ATT CAC GCC GCT AAC AAA CTC GCT AGC AAG CAC CAA CGT CTT CAT CTT         262
Ile His Ala Ala Asn Lys Leu Ala Ser Lys His Gln Arg Leu His Leu
260             265                 270                     275

AAT TCC CTC TCC ACC AAA TTC CCT CGT TGC GAT ATC TGC CAA GAG AAG         310
Asn Ser Leu Ser Thr Lys Phe Pro Arg Cys Asp Ile Cys Gln Glu Lys
                280                 285                 290

GCA GCT TTC ATT TTC TGT GTA GAG GAT AGA GCT CTG CTT TGC AGG GAC         358
Ala Ala Phe Ile Phe Cys Val Glu Asp Arg Ala Leu Leu Cys Arg Asp
            295             300                 305

TGC GAT GAA TCC ATC CAC GTG GCT AAT TCT CGA TCT GCT AAT CAC CAG         406
Cys Asp Glu Ser Ile His Val Ala Asn Ser Arg Ser Ala Asn His Gln
        310             315                 320

AGG TTC TTA GCC ACT GGG ATC AAA GTA GCT CTG ACC TCA ACT ATA TGT         454
Arg Phe Leu Ala Thr Gly Ile Lys Val Ala Leu Thr Ser Thr Ile Cys
325             330                 335

AGT AAA GAA ATT GAG AAG AAT CAA CCT GAG CCT TCC AAC AAC CAA CAG         502
Ser Lys Glu Ile Glu Lys Asn Gln Pro Glu Pro Ser Asn Asn Gln Gln
340             345                 350                     355

AAG GCT AAT CAG ATT CCT GCT AAA TCC ACA AGC CAG CAG CAA CAA CAA         550
Lys Ala Asn Gln Ile Pro Ala Lys Ser Thr Ser Gln Gln Gln Gln Gln
                360                 365                 370

CCT TCT TCT GCT ACT CCA CTT CCC TGG GCT GTT GAC GAT TTC TTT CAC         598
Pro Ser Ser Ala Thr Pro Leu Pro Trp Ala Val Asp Asp Phe Phe His
            375             380                 385

TTC TCT GAT ATT GAA TCC ACC GAC AAG AAA GGA CAG CTT GAT CTT GGG         646
Phe Ser Asp Ile Glu Ser Thr Asp Lys Lys Gly Gln Leu Asp Leu Gly
        390             395                 400

GCA GGG GAG TTG GAT TGG TTT TCA GAC ATG GGA TTC TTC GGT GAT CAG         694
Ala Gly Glu Leu Asp Trp Phe Ser Asp Met Gly Phe Phe Gly Asp Gln
405             410                 415

ATT AAT GAC AAG GCT CTT CCT GCA GCT GAA GTT CCT GAG CTT TCT GTT         742
Ile Asn Asp Lys Ala Leu Pro Ala Ala Glu Val Pro Glu Leu Ser Val
420             425                 430                     435

TCG CAT TTA GGT CAT GTT CAT TCA TAC AAA CCT ATG AAG TCA AAT GTT         790
Ser His Leu Gly His Val His Ser Tyr Lys Pro Met Lys Ser Asn Val
                440                 445                 450

TCA CAC AAG AAG CCG AGG TTT GAG ACC AGA TAT GAT GAT GAT GAT GAG         838
Ser His Lys Lys Pro Arg Phe Glu Thr Arg Tyr Asp Asp Asp Asp Glu
            455             460                 465

GAA CAC TTC ATT GTC CCT GAT CTT GGC TAA AAAGCTATAT GTAATCTATG           888
Glu His Phe Ile Val Pro Asp Leu Gly  *
        470             475

TGTAGACATT CTTCAATGTA AAAGAACAAA CAAGAAACCT ATCTGCATGT GTGGAGTTAA       948

TGTCATATAC ATTTAGTTTT TGTCTTAAGT TGTGTAAGAT ATGTTGAGAG CTTATAACAA      1008

ATGTCTGTGT TTGAGTTAAA AAAAA                                            1033
```

( 2 ) INFORMATION FOR SEQ ID NO:4:

(i) SEQUENCE CHARACTERISTICS:
    (A) LENGTH: 248 amino acids
    (B) TYPE: amino acid
    (D) TOPOLOGY: linear (ii) MOLECULE TYPE: protein (xi) SEQUENCE DESCRIPTION: SEQ ID NO:4:

| Met | Lys | Ile | Gln | Cys | Asp | Val | Cys | Glu | Lys | Ala | Pro | Ala | Thr | Val | Ile |
|---|---|---|---|---|---|---|---|---|---|---|---|---|---|---|---|
| 1 | | | | 5 | | | | | 10 | | | | | 15 | |

| Cys | Cys | Ala | Asp | Glu | Ala | Ala | Leu | Cys | Pro | Gln | Cys | Asp | Ile | Glu | Ile |
|---|---|---|---|---|---|---|---|---|---|---|---|---|---|---|---|
| | | | 20 | | | | 25 | | | | | 30 | | | |

| His | Ala | Ala | Asn | Lys | Leu | Ala | Ser | Lys | His | Gln | Arg | Leu | His | Leu | Asn |
|---|---|---|---|---|---|---|---|---|---|---|---|---|---|---|---|
| | | 35 | | | | | 40 | | | | 45 | | | | |

| Ser | Leu | Ser | Thr | Lys | Phe | Pro | Arg | Cys | Asp | Ile | Cys | Gln | Glu | Lys | Ala |
|---|---|---|---|---|---|---|---|---|---|---|---|---|---|---|---|
| | 50 | | | | | 55 | | | | | 60 | | | | |

| Ala | Phe | Ile | Phe | Cys | Val | Glu | Asp | Arg | Ala | Leu | Leu | Cys | Arg | Asp | Cys |
|---|---|---|---|---|---|---|---|---|---|---|---|---|---|---|---|
| 65 | | | | | 70 | | | | | 75 | | | | | 80 |

| Asp | Glu | Ser | Ile | His | Val | Ala | Asn | Ser | Arg | Ser | Ala | Asn | His | Gln | Arg |
|---|---|---|---|---|---|---|---|---|---|---|---|---|---|---|---|
| | | | | 85 | | | | | 90 | | | | | 95 | |

| Phe | Leu | Ala | Thr | Gly | Ile | Lys | Val | Ala | Leu | Thr | Ser | Thr | Ile | Cys | Ser |
|---|---|---|---|---|---|---|---|---|---|---|---|---|---|---|---|
| | | | 100 | | | | | 105 | | | | 110 | | | |

| Lys | Glu | Ile | Glu | Lys | Asn | Gln | Pro | Glu | Pro | Ser | Asn | Asn | Gln | Gln | Lys |
|---|---|---|---|---|---|---|---|---|---|---|---|---|---|---|---|
| | | 115 | | | | | 120 | | | | | 125 | | | |

| Ala | Asn | Gln | Ile | Pro | Ala | Lys | Ser | Thr | Ser | Gln | Gln | Gln | Gln | Gln | Pro |
|---|---|---|---|---|---|---|---|---|---|---|---|---|---|---|---|
| | 130 | | | | | 135 | | | | | 140 | | | | |

| Ser | Ser | Ala | Thr | Pro | Leu | Pro | Trp | Ala | Val | Asp | Phe | Phe | His | Phe |
|---|---|---|---|---|---|---|---|---|---|---|---|---|---|---|
| 145 | | | | | 150 | | | | | 155 | | | | 160 |

| Ser | Asp | Ile | Glu | Ser | Thr | Asp | Lys | Lys | Gly | Gln | Leu | Asp | Leu | Gly | Ala |
|---|---|---|---|---|---|---|---|---|---|---|---|---|---|---|---|
| | | | | 165 | | | | | 170 | | | | | 175 | |

| Gly | Glu | Leu | Asp | Trp | Phe | Ser | Asp | Met | Gly | Phe | Phe | Gly | Asp | Gln | Ile |
|---|---|---|---|---|---|---|---|---|---|---|---|---|---|---|---|
| | | | 180 | | | | | 185 | | | | | 190 | | |

| Asn | Asp | Lys | Ala | Leu | Pro | Ala | Ala | Glu | Val | Pro | Glu | Leu | Ser | Val | Ser |
|---|---|---|---|---|---|---|---|---|---|---|---|---|---|---|---|
| | | 195 | | | | | 200 | | | | | 205 | | | |

| His | Leu | Gly | His | Val | His | Ser | Tyr | Lys | Pro | Met | Lys | Ser | Asn | Val | Ser |
|---|---|---|---|---|---|---|---|---|---|---|---|---|---|---|---|
| | 210 | | | | | 215 | | | | | 220 | | | | |

| His | Lys | Lys | Pro | Arg | Phe | Glu | Thr | Arg | Tyr | Asp | Asp | Asp | Glu | Glu |
|---|---|---|---|---|---|---|---|---|---|---|---|---|---|---|
| 225 | | | | | 230 | | | | | 235 | | | | 240 |

| His | Phe | Ile | Val | Pro | Asp | Leu | Gly |
|---|---|---|---|---|---|---|---|
| | | | | 245 | | | |

(2) INFORMATION FOR SEQ ID NO:5:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (iii) HYPOTHETICAL: NO (xi) SEQUENCE DESCRIPTION: SEQ ID NO:5:

CCCCTCGAGT CACACAGGAG CCA        23

GENES CONFERRING SALT TOLERANCE AND THEIR USES

This invention was made with Government support under Grant No. 90-58-284, awarded by the National Science Foundation. The Government has certain rights in this invention.

FIELD OF THE INVENTION

The present invention relates generally to plant molecular biology. In particular, it relates to nucleic acids and methods for conferring salt tolerance on plants and other organisms.

BACKGROUND OF THE INVENTION

Because of limited water supplies and the widespread use of irrigation, the soils of many cultivated areas have become increasingly salinized. In particular, modern agricultural practices such as irrigation impart increasing salt concentrations when the available irrigation water evaporates and leaves previously dissolved salts behind. As a result, the development of salt tolerant cultivars of agronomically important crops has become important in many parts of the world.

Dissolved salts in the soil increase the osmotic pressure of the solution in the soil and tend to decrease the rate at which water from the soil will enter the roots. If the solution in the soil becomes too saturated with dissolved salts, the water may actually be withdrawn from the plant roots. Thus the plants slowly starve though the supply of water and dissolved nutrients may be more than ample. Also, elements such as sodium are known to be toxic to plants when they are taken up by the plants.

Salt tolerant plants can facilitate use of marginal areas for crop production, or allow a wider range of sources of irrigation water. Traditional plant breeding methods have, thus far, not yielded substantial improvements in salt tolerance and growth of crop plants. In addition, such methods require long term selection and testing before new cultivars can be identified.

Genetic engineering and other methods have been used in attempts to improve crop plants by understanding the genetic basis for salt tolerance. For instance, considerable effort has been directed to the selection of salt tolerant plant cells and callus in vitro (see, e.g., Dix *The Plant Journal* 3:309–313 (1993)). A major barrier in the improvement of salt tolerance in crops is the poor understanding of the specific genes that have the potential of increasing salt tolerance (reviewed in Serrano et al., *Crit. Rev. Plant Sci.* 13:121–138 (1994)).

Genes associated with adaptation to salt stress have been identified in yeast. Serrano and coworkers have identified two genes, HAL1 (Gaxiola et al. *EMBO J.* 11:3157–3164 (1992)) and HAL2 (Glaser et al. *EMBO J.* 12:3105–3110 (1993)) in *Saccharomyces cerevisiae* by selecting for genes whose overexpression leads to improved growth on salt. A HAL1 homolog is present in plants where it is induced by NaCl and abscisic acid, a plant hormone known to mediate adaptation of plants to osmotic stress Murguia et al., *Science* 267:232–234 (1995)).

Another gene, calcineurin, or phosphoprotein phosphatase type 2B (PP2B), is a calmodulin-regulated enzyme found in many organisms including yeast. Although its physiological functions are not well understood, it is known that yeast strains which do not contain active calcineurin proteins are more sensitive to growth inhibition by salt than are wild-type strains. Bacterial genes associated with salt tolerance have also been identified. Tarczynski et al., *Science* 259:508–510 (1993)).

Despite the efforts toward cloning genes conferring tolerance to saline conditions, no single salt tolerance plant gene has been identified. The present invention addresses these and other needs.

SUMMARY OF THE INVENTION

The present invention provides isolated nucleic acid constructs comprising polynucleotide sequences which confer salt tolerance on plants. Two preferred polynucleotides, STZ and STO, are shown in SEQ. ID. Nos. 1 and 3, respectively. The polynucleotides of the invention may be operably linked to promoters to provide expression in transgenic plants. Thus, the invention also provides transgenic plant comprising a recombinant expression cassette including the polynucleotides of the invention.

The invention further provides methods of conferring salt tolerance on a plant. The methods comprise introducing into the plant a recombinant expression cassette comprising a plant promoter operably linked to an STZ or STO polynucleotide sequence.

Definitions

The term "plant" includes whole plants, plant organs (e.g., leaves, stems, roots, etc.), seeds and plant cells and progeny of same. The class of plants which can be used in the methods of the invention is generally as broad as the class of higher plants amenable to transformation techniques, including both monocotyledonous and dicotyledonous plants.

A "heterologous sequence" is one that originates from a foreign species, or, if from the same species, is substantially modified from its original form. For example, a heterologous promoter operably linked to structural gene is from a species different from that from which the structural gene was derived, or, if from the same species, is substantially modified from its original form.

An "STZ polynucleotide sequence" or an "STO polynucleotide sequence" is a subsequence or full length polynucleotide sequence of an STZ or an STO gene, respectively. Such polynucleotides, when present in a transgenic plant, yeast, fungus, or other organisms, confer salt tolerance. Exemplary polynucleotides of the invention include the coding region of SEQ ID No.:1 (STZ) and SEQ ID No.:3 (STO). The coding region of an STZ polynucleotide (exclusive of introns) is typically at least about nucleotides to about 200 nucleotides in length, usually from about 300 to about 684 nucleotides. The coding region of an STO polynucleotide (exclusive of introns) is typically at least about nucleotides to about 200 nucleotides in length, usually from about 300 to about 747 nucleotides.

An "STZ polypeptide" or an "STO polypeptide" is a gene product of an STZ or an STO polynucleotide sequence, respectively. Such polypeptides have the ability to confer tolerance to saline conditions on plants, yeast, fungi or other organisms. STZ polypeptides are characterized by sequence identity with a family of putative zinc finger containing transcription factor isolated from Petunia (Takatsuji et al., *The Plant Cell* 6:947–958 (1994)). Exemplary STZ and STO polypeptides of the invention are SEQ ID No.:2 (STZ) and SEQ ID No.:4 (STO).

In the expression of transgenes one of skill will recognize that the inserted polynucleotide sequence need not be identical and may be "substantially identical" to a sequence of the gene from which it was derived. As explained below, these variants are specifically covered by this term.

In the case where the inserted polynucleotide sequence is transcribed and translated to produce a functional STZ or STO polypeptide, one of skill will recognize that because of codon degeneracy, a number of polynucleotide sequences will encode the same polypeptide. These variants are specifically covered by the terms "STZ polynucleotide sequence" or "STO polynucleotide sequence". In addition, the terms specifically include those full length sequences substantially identical (determined as described below) with an STZ or STO gene sequence and that encode proteins that retain the function of the encoded proteins. Thus, in the case of the Arabidopsis STZ and STO genes disclosed here, the above term includes variant polynucleotide sequences which have substantial identity with the sequences disclosed here and which encode proteins capable of conferring salt tolerance on a transgenic plant comprising the sequence.

Two polynucleotides or polypeptides are said to be "identical" if the sequence of nucleotides or amino acid residues, respectively, in the two sequences is the same when aligned for maximum correspondence as described below. The term "complementary to" is used herein to mean that the complementary sequence is identical to all or a portion of a reference polynucleotide sequence.

Sequence comparisons between two (or more) polynucleotides or polypeptides are typically performed by comparing sequences of the two sequences over a segment or "comparison window" to identify and compare local regions of sequence similarity. The segment used for purposes of comparison may be at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman *Adv. Appl. Math.* 2: 482 (1981), by the homology alignment algorithm of Needleman and Wunsch *J. Mol. Biol.* 48:443 (1970), by the search for similarity method of Pearson and Lipman *Proc. Natl. Acad. Sci. (U.S.A.)* 85: 2444 (1988), by computerized implementations of these algorithms (GAP, BESTFIT, FASTA, and TFASTA in the Wisconsin Genetics Software Package, Genetics Computer Group (GCG), 575 Science Dr., Madison, Wis.), or by inspection. "Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 60% sequence identity, preferably at least 80%, more preferably at least 90% and most preferably at least 95%, compared to a reference sequence using the programs described above (preferably BESTFIT) using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%, preferably at least 60%, more preferably at least 90%, and most preferably at least 95%. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Another indication that nucleotide sequences are substantially identical is if two molecules hybridize to each other under stringent conditions. Stringent conditions are sequence dependent and will be different in different circumstances. Generally, stringent conditions are selected to be about 5° C. to about 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code.

As used herein, a homolog of a particular STZ or STO gene (e.g., the Arabidopsis STZ and STO genes disclosed here) is a second gene (either in the same species or in a different species) which has a polynucleotide sequence of at least 50 contiguous nucleotides which are substantially identical (determined as described above) to a sequence in the first gene. It is believed that, in general, homologs share a common evolutionary past.

BRIEF DESCRIPTION OF THE DRAWINGS

FIGS. 2A–B show that expression of STO or STZ increases tolerance to LiCl of wild-type yeast. Wild-type strain (YPH499) transformed with plasmids carrying the sequence coding for STO (pVL36), STZ (pVL35) or GAL1-

Figure 1A:
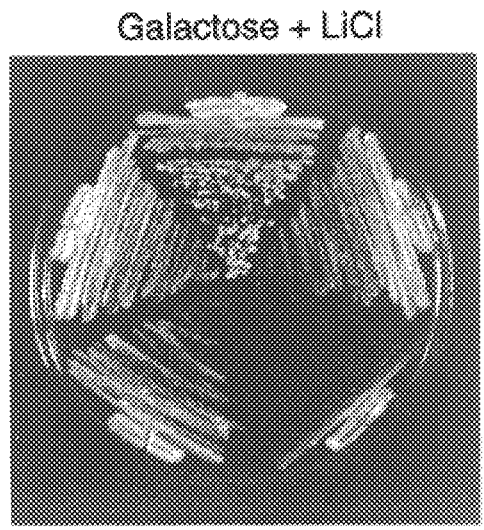
FIGS. 1A–1C show that expression of STO or STZ increases tolerance to LiCl of calcineurin mutant strains. Strains MCY300-1 (cna1 cna2) (FIG. 1A) or DD12 (cnb1) (FIG. 1C) harboring (clockwise from top) an STO-expression plasmid (pVL36), an STZ-expression plasmid (pVL35), a vector control (pVL15), or the GAL1-CNA2 plasmid (pVL14) and the isogenic wild-type strain (YPH499) containing the vector control (pVL15) were streaked onto YPGalRaf (galactose) medium containing 180 mM LiCl, or onto YPD (glucose) medium supplemented with 200 mM LiCl (FIG. 1B). Plates were photographed after incubating them for 8 days at 30° C.

CNA2 (pVL14) or containing a vector control (pVL15) were streaked on YPGalRaf (galactose) medium containing 0 (FIG. 2B) or 260 mM LiCl (FIG. 2A) and were incubated for 3 days (galactose, no LiCl) or 8 days (galactose+LiCl) at 30° C.

DESCRIPTION OF THE PREFERRED EMBODIMENTS

This invention relates to genes (the STZ and STO genes) capable of conferring salt tolerance on transgenic organisms. Nucleic acid sequences from STZ and STO genes can be used to confer salt tolerance on plants and other organisms. The invention has use over a broad range of types of plants, including species from the genera Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, vigna, and, Zea.

The salt tolerant transgenic plants or other organisms of the invention are capable of growing under saline conditions which inhibit the growth of at least 95% of the parent, non-salt tolerant organisms from which the salt tolerant transgenic organisms are derived. Typically, the growth rate of salt tolerant organisms of the invention will be inhibited by less than 50%, preferably less than 30%, and most preferably will have a growth rate which is not significantly inhibited by a growth medium containing water soluble inorganic salts which inhibits growth of at least 95% of the parental, non-salt tolerant organisms.

Salt concentration under which organisms of the invention are capable of growing are typically between about 20 mM and about 500 mM, often between about 40 mM and about 300 mM.

In the case of plants, exemplary water-soluble inorganic salts commonly encountered in saline soils are alkali metal salts, alkaline earth metal salts, and mixtures of alkali metal salts and alkaline earth metal salts. These commonly include sodium sulfate, magnesium sulfate, calcium sulfate, sodium chloride, magnesium chloride, calcium chloride, potassium chloride and the like. Soil conductivity is typically used to determine the degree of salinity of a particular soil. Such soil conductivity measurement can be made in situ by standard procedures using a soil contacting Wenner Array four probe resistivity meter or other equivalent device.

The Example section below, which describes the isolation and characterization of STZ and STO genes in Arabidopsis, is exemplary of a general approach for isolating salt tolerance genes of the invention. The isolated genes can then be used to construct recombinant vectors for transferring gene capable of conferring salt tolerance to transgenic plants.

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., (1989).

The isolation of STZ and STO and related salt tolerance genes may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as leaf and a cDNA library which contains the gene transcript is prepared from the mRNA. Alternatively, cDNA may be prepared from mRNA extracted from other tissues in which STZ and STO genes or their homologs are expressed.

The cDNA or genomic library can then be screened using a probe based upon the sequence of a cloned STZ or STO gene such as the Arabidopsis genes disclosed here. Probes may be used to hybridize with genomic DNA or cDNA sequences to isolate homologous genes in the same or different plant species.

Alternatively, the nucleic acids of interest can be amplified from nucleic acid samples using amplification techniques. For instance, polymerase chain reaction (PCR) technology to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying salt tolerance genes from plant tissues are generated from comparisons of the sequences provided herein. For a general overview of PCR see *PCR Protocols: A Guide to Methods and Applications*. (Innis, M, Gelfand, D., Sninsky, J. and White, T., eds.), Academic Press, San Diego (1990), incorporated herein by reference.

Polynucleotides may also be synthesized by well-known techniques as described in the technical literature. See, e.g., Carruthers et al., *Cold Spring Harbor Symp. Quant. Biol.* 47:411–418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

Isolated sequences prepared as described herein can then be used to confer salt tolerance in desired plants, yeast or other fungi. One of skill will recognize that the nucleic acid encoding a functional STZ or STO protein (e.g., SEQ. ID. Nos. 2 and 4) need not have a sequence identical to the exemplified gene disclosed here. In addition, the polypeptides encoded by the genes, like other proteins, have different domains which perform different functions. Thus, the gene sequences need not be full length, so long as the desired functional domain of the protein is expressed. For instance, the STZ proteins of the invention comprise zinc finger motif. Modified protein chains can also be readily designed utilizing various recombinant DNA techniques well known to those skilled in the art. For example, the chains can vary from the naturally occurring sequence at the primary structure level by amino acid substitutions, additions, deletions, and the like. Modification can also include swapping domains from the proteins of the invention with related domains from other plant genes. These modifications can be used in a number of combinations to produce the final modified protein chain.

To use isolated polynucleotide sequences of the invention in the above techniques, recombinant DNA vectors suitable for transformation of plants, yeast or fungi are prepared.

Expression in Yeast and Fungi

Recombinant expression of proteins in yeast is well known and described. *Methods in Yeast Genetics*, Sherman, F., et al., Cold Spring Harbor Laboratory, (1982) is a well recognized work describing the various methods available to produce recombinant polypeptides in yeast. The genes of the invention can be used to confer salt tolerance on yeast strains used in baking, brewing, or recombinant production of desired heterologous proteins. Typically, yeast strain that are currently used to produce food components (e.g., Kluyveromyces species) are used.

A number of well known yeast expression plasmids can be used as vectors. A gene of interest can be fused to any of the promoters in various yeast vectors. For instance, suitable vectors are described in the literature (Botstein, et al., 1979, Gene, 8:17–24; Broach, et al., 1979, Gene, 8:121–133).

To prepare an expression vector suitable for expression of the genes of the invention in yeast, the coding region of an STZ or STO polynucleotide is inserted into a yeast expression vector operably linked to a promoter for high-level transcription (for example the GAL1 promoter, the triose phosphate isomerase promoter, the alcohol dehydrogenase promoter or any other similar promoter sequence known to those skilled in the art). The vector should also contain standard sequences necessary for replication and maintenance of the plasmid in yeast, including, but not limited to one or more of the following: an origin of replication or autonomously replicating sequence; a centromere region; a selectable marker suitable for selection of clones harboring plasmids in the particular strain one desires to make salt tolerant.

Two procedures are generally used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by J. D. Beggs, 1978, Nature (London), 275:104–109; and Hinnen, A., et al., 1978, Proc. Natl. Acad. Sci. USA, 75:1929–1933. The second procedure does not involve removal of the cell wall. Instead the cells are treated with lithium chloride or acetate and PEG and put on selective plates (Ito, H., et al., 1983, J. Bact., 153:163–168).

Techniques for transforming other fungi are well known in the literature, and have been described, for instance, by Beggs (*Nature* 275:104–108 (1978)), Hinnen et al. (*Proc. Natl. Acad. Sci. USA* 75: 1929–1933, 1978), Yelton et al. (*Proc. Natl. Acad. Sci. USA* 81: 1740–1747, 1984), Russell (*Nature* 301: 167–169, 1983) and U.S. Pat. No. 4,935,349. Expression in fungi can be accomplished using for example, Aspergillus, and the like.

Expression in Plants

Techniques for transforming a wide variety of higher plant species are well known and described in the technical and scientific literature. See, for example, Weising et al. *Ann. Rev. Genet*. 22:421–477 (1988).

A DNA sequence coding for the desired STZ or STO polypeptide, for example a cDNA or a genomic sequence encoding a full length protein, will be used to construct a recombinant expression cassette which can be introduced into the desired plant. An expression cassette will typically comprise the desired polynucleotide operably linked to transcriptional and translational initiation regulatory sequences which will direct the transcription of the sequence from the gene in the intended tissues of the transformed plant.

For example, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'- promoter derived from T-DNA of *Agrobactenium tumafaciens*, and other transcription initiation regions from various plant genes known to those of skill.

Alternatively, the plant promoter may direct expression of the gene in a specific tissue or may be otherwise under more precise environmental or developmental control. Such promoters are referred to here as "inducible" or "developmentally regulated" promoters.

Examples of promoters under developmental control include promoters that initiate transcription only in certain tissues, such as leaves, roots, fruit, seeds, or flowers. The operation of a promoter may also vary depending on its location in the genome. Thus, an inducible promoter may become fully or partially constitutive in certain locations.

The endogenous promoters from the STZ and STO genes of the invention can also be used to direct expression of the genes. These promoters can also be used to direct expression of heterologous structural genes. Thus, the promoters can be used in recombinant expression cassettes to drive expression of genes conferring other desirable traits on plants, such as resistance to other environmental stresses.

The cDNA clones described here can be used to identify corresponding genomic clones in a genomic library. To identify the promoters, the 5' portions of the genomic clones are analyzed for sequences characteristic of promoter sequences. For instance, promoter sequence elements include the TATA box consensus sequence (TATAAT), which is usually 20 to 30 base pairs upstream of the transcription start site. In plants, further upstream from the TATA box, at positions −80 to −100, there is typically a promoter element with a series of adenines surrounding the trinucleotide G (or T) N G. J. Messing et al., in *Genetic Engineering in Plants*, pp. 221–227 (Kosage, Meredith and Hollaender, eds. 1983). Generally, functional promoter sequences can be identified at least about 600 bp upstream, usually about 2–3 kb, from the translation start site.

If proper polypeptide expression is desired, a polyadenylation region at the 3'-end of the coding region should be included. The polyadenylation region can be derived from the natural gene, from a variety of other plant genes, or from T-DNA.

The vector comprising the sequences from an STZ or STO gene will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

Such DNA constructs may be introduced into the genome of the desired plant host by a variety of conventional techniques. For example, the DNA construct may be introduced directly into the genomic DNA of the plant cell using techniques such as electroporation, PEG poration, particle bombardment and microinjection of plant cell protoplasts or embryogenic callus, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al. *Embo J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987). Using a number of approaches, cereal species such as rye (de la Pena et al., *Nature* 325:274–276 (1987)), corn (Rhodes et al., *Science* 240:204–207 (1988)), and Arabidopsis (Shimamoto et al., *Nature* 338:274–276 (1989) by electroporation; Li et al. *Plant Cell Rep.* 12:250–255 (1993) by ballistic techniques) can be transformed.

*Agrobacterium tumefaciens*—meditated transformation techniques are well described in the scientific literature. See, for example Horsch et al. *Science* 233:496–498 (1984), and Fraley et al. *Proc. Natl. Acad. Sci. USA* 80:4803 (1983). Although Agrobacterium is useful primarily in dicots, certain monocots can be transformed by Agrobacterium. For instance, Agrobacterium transformation of rice is described by Hiei et al, *Plant J.* 6:271–282 (1994).

After selecting the transformed cells, the expression of the gene of the invention can be confirmed by standard techniques. Simple detection of mRNA encoded by the inserted DNA can be achieved by well known methods in the art, such as Northern blot hybridization. The inserted sequence can be identified by Southern blot hybridization, as well.

In addition, the transformed cells with the salt tolerance phenotype can be selected in vitro by culturing the cells on media containing increased inorganic salt concentrations. For instance, callus tissue can be transferred to standard tissue culture media supplemented with inorganic salts described above, typically sodium chloride. The salt concentration will typically be greater than about 80 mM, preferably about 140 mM, to about 30 mM. The concentration will vary depending upon the sensitivity of the plant being transformed.

Transformed plant cells which are derived by any of the above transformation techniques can be cultured to regenerate a whole plant which possesses the transformed genotype and thus display the salt tolerant phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture, Handbook of Plant Cell Culture*, pp. 124–176, MacMillilan Publishing Company, New York, 1983; and Binding, *Regeneration of Plants, Plant Protoplasts*, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

The methods of the present invention are particularly useful for incorporating the polynucleotides of the invention into transformed plants in ways and under circumstances which are not found naturally. In particular, the STZ or STO polypeptides may be expressed at times or in quantities which are not characteristic of natural plants.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The effect of the modification of STZ or STO gene expression can be measured by detection of increases or decreases in mRNA levels using, for instance, Northern blots. In addition, the phenotypic effects of gene expression can be detected by measuring salt tolerance in plants. Suitable assays for determining resistance are described below.

The following Examples are offered by way of illustration, not limitation.

EXAMPLE 1

Yeast strains which do not contain active calcineurin proteins (protein phosphatase 2B, or PP2B) have been shown to be more sensitive to growth inhibition by salt than are wild-type strains. In particular these strains are sensitive to elevated concentrations of Li+ and Na+ ions. Active calcineurin in yeast is an oligomer which includes two calcineurin-specific subunits, CNA and CNB, and calmodulin. In yeast there are two genes encoding the CNA subunit, CNA1 and CNA2, and one gene encoding the CNB subunit, the CNB gene. These strains were transformed with clones of a cDNA library prepared from *Arabidopsis thaliana* to identify clones which corrected the salt sensitive mutant phenotype.

Experimental Procedures
Yeast Strains and Culture conditions

Yeast strains used were derivatives of YPH499 (Sikorski et al., *Genetics* 122:19–27 (1989)) referred to as wild type, wt. Construction of cna1_1::hisG cna2_1::HIS3 (referred to as cna1 cna2) and cnb1_1::LEU2 (referred to as cnb1) null mutants were as previously described Cyert et al. *Mol. Cell. Biol.* 12:3460–3469 (1992); Cyert et al. *Proc. Natl. Acad. Sci. USA* 88:7376–7380 (1991)).

Rich medium (YP) consisted of 2% Difco yeast extract, 1% bacto-peptone, 50 µg/ml adenine sulfate supplemented with either 2% dextrose (YPD), or 2% galactose, 2% raffinose (YPGalRaf). Synthetic complete minus uracil medium (SC-Ura) was prepared as described by Sherman et al. Methods in yeast genetics (Cold Spring Harbor, N.Y.: Cold Spring Harbor Lab. 1986) except that twice the recommended levels of nutritional supplements were used.

Unless otherwise specified yeast transformations were performed as described by Elble et al. *Biotechniques* 13:18–20 (1992).

Screening for Arabidopsis cDNA Clones that Complement the Salk-Sensitive Phenotype of Calcineunn Mutants Clones that rescued the salt-sensitive phenotype of calcineurin null mutants were isolated from an Arabidopsis cDNA library constructed in 1YES (a gift from John Mulligan, Stanford University; Elledge et al. *Proc. Natl. Acad. Sci. USA* 88:1731–1735 (1991)). This phage library was converted into a plasmid (URA3 CEN4 ARS1) library using the cre-lox site-specific recombination system Elledge et al. The plasmid library, in which inserts are transcribed under control of the GAL1-promoter, was transformed into the cna1 cna2 strain and cnb1 cells essentially as described by Gietz et al. *Nucleic Acids Res.* 20:1425 (1992) and cells were plated on SD-Ura (SC-Ura medium containing dextrose). Ura$^+$ colonies were pooled, incubated in 2% Gal, 50 mM MES pH 5.5 for 3 h, and ~5×10$^5$ cells were plated on YPGalRaf medium supplemented with 200 mM LiCl and incubated for 6 d at 30° C. A total of 1×10$^6$ transformants representing 5×10$^5$ independent transformants were screened in each mutant background.

Plasmids were recovered from salt-resistant Ura$^+$ colonies that continued to grow on YPGalRaf medium supplemented with 260 mM LiCl but not on YPD medium supplemented with 200 mM LiCl by transformation of *E. coli* cells (Hoffman in *Current Protocols in Molecular Biology*, Ausubel et al. eds (New York: Wiley pp. 13.11.1–13.11.4 1993)). Isolated plasmids were reintroduced into fresh preparations of the mutant strain used for their isolation and were retested for galactose-dependent growth on medium containing 200 mM LiCl. 18 positive isolates were identified of which pVL35 and pVL37 contain STZ cDNA inserts, and pVL36 and pVL38 contain STO cDNA inserts.

As a positive control to screen for salt-resistance, a plasmid carrying the CNA2 coding sequence under the GAL1 promoter was constructed as follows. A BamHI/HindIII fragment containing the CNA2 coding region was isolated from YEp352-CNA2 (YEp-CNA2) and inserted into these same sites of pBluescript KS+(Stratagene, La Jolla), creating pVL10. An XhoI site was engineered 5' of the CNA2 coding sequence by the polymerase chain reaction (PCR) using standard procedures and the T3 primer of pBluescript (KS−) and a primer based on the 5' untranslated region of the CNA2 gene 5' CCC CTC GAG TCA CAC AGG AGC CA 3' (SEQ ID No.:5) (the XhoI site is underlined). The PCR product was inserted into the EcoRV site of pBluescript KS+, resulting in pVL12. A 2.7 kb XhoI fragment (the 3' XhoI site derives from the multi-linker of the cloning vector) that includes the CNA2 coding region was transferred from pVL12 into the XhoI site of pVL11, an isolate from the plasmid-rescued 1YES library, replacing the insert of this clone. The resulting plasmid, pVL14 (URA3 CEN4 ARS1) and referred to as pGAL1-CNA2, contains the GAL1-promoted CNA2 sequence. An empty vector was constructed as a negative control by removing the insert in pVL11 with XhoI followed by religation, producing pVL15.

DNA Manipulation and Sequencing

Subclones were produced by standard techniques (Crouse, *Methods Enzymol.* 101:78–89 (1983)). Single-stranded templates were produced from plasmid subclones. Single-stranded templates or double-stranded plasmids were sequenced using the dideoxynucleotide-termination method and Sequenase polymerase (United States Biochemical, Cleveland). Both strands of selected cDNAs were completely sequenced. Sequence analysis was performed using the sequence analysis software package of the Genetics Computer Group (Madison, Wis.).

Plant Material and NaCl treatments

Genomic DNA and RNA were prepared from *Arabidopsis thaliana* (L.) Heynh. ecotypes Landsberg erecta and Colombia grown at 20°–25° C. under continuous fluorescent and incandescent light as described Kranz, Arabidopsis Information Service, v. 24: Genetic Resources in Arabidopsis (Frankfurt, Germany: Arabidopsis Information Service, 1987). For salt-treatment experiments, surface sterilized Arabidopsis seeds were sown in Petri dishes (100×25 mm) containing 20 ml germination media (Valvekens, et al., *Proc. Natl. Acad. Sci USA* 85:5536–5540 (1988)) and were grown for 12 days at 23° C. under continuous fluorescent light. The concentration of NaCl in the medium was then increased to 0, 80, 140, 220 mM (expected concentrations at equilibrium following diffusion) by adding a concentrated solution of NaCl to the medium surface as described by Lehle et al., *Physiologia Plantarum* 84:223–228 (1992). 30 h after exposure to NaCl, plants were harvested and frozen under liquid nitrogen.

DNA and RNA Blot Analysis

Arabidopsis RNA was isolated according to Rochester et al., *EMBO J.* 5:451–458 (1986). RNA was fractionated on 1.2% agarose/formaldehyde gels and transferred to nylon membranes overnight using 10× SSPE (1× SSPE is 150 mM NaCl, 10 mM sodium phosphate, 1 mM NaCl, pH 7.4). One ug/ml of ethidium bromide was included in gels to visualize the 18 S and 26 S ribosomal RNAs for quantitative purposes. The filters were hybridized overnight in 50% deionized formamide, 3× SSPE SSPE, 0.5% SDS, 4× Denhardt's (1× Denhardt's solution is 0.02% each Ficoll, bovine serum albumin, and polyvinylpyrrolidone), 50 μg/ml tRNA (Sigma) at 45° C. The final wash buffer was 0.3× SSPE, 0.1% SDS at 65° C., unless otherwise indicated. Intensity of bands was quantitated using a BAS 1000 phosphorimager.

Arabidopsis genomic DNA was isolated as described by Dellaporta *Plant Mol. Biol. Rep.* 1:19–21 (1983), digested with BamHI, EcoRI, or HindIII, fractionated on 0.8% agarose gels and transferred to nylon membranes. Hybridization was performed in 2× SSPE, 0.1% SDS, 50 μg/ml tRNA, 2× Denhardt's solution at 65° C. The final washes were as described for RNA blot analysis. Similar hybridization and wash conditions were used to determine the identity of some of the cDNA clones.

The same cDNA inserts were used as hybridization probes for DNA and RNA blot analyses. The fragment used to prepare the "STZ probe" was a 0.65 kb XhoI/EcoRI fragment of one of the STZ cDNA clones (pVL37) and is missing 243 bases of 3' coding sequence. The XhoI site is a carry-over from the 5' linker used to prepare the library and the EcoRI site corresponds to an internal site in the STZ coding region. The fragment used to prepare the "STO probe" was a 1.1 kb XhoI fragment of one of the STO cDNA clones (pVL38) and includes the entire STO cDNA insert between the two AhoI polylinker sites. Hybridizations were performed with 2–3×10$^6$ cpm/ml of cDNA inserts labeled with $^{32}$P by the random priming method.

Results

Isolation and nucleotide analysis of Arabidopsis cDNA clones that confer salt resistance on yeast calcineurin mutants To identify Arabidopsis clones that rescue the salt-sensitive phenotype of yeast calcineurin mutants, we transformed cna1 cna2 double null mutants and cnb1 null mutants with an Arabidopsis cDNA library under the control of the galactose-inducible GAL1 promoter. To select for salt-resistant colonies, transformants were plated under inducing conditions on rich medium containing LiCl. Since the frequency of spontaneous reversion to salt resistance was high under these conditions (~1 in 10,000), transformants were first tested for uracil prototrophy. Uracil prototrophs were then tested for their ability to grow on medium containing LiCl and galactose, but not on medium containing LiCl and glucose.

In this screen, 34 of 111 salt-resistant colonies showed galactose-dependent salt tolerance in the cna1 cna2 background, whereas 39 of 104 showed this growth phenotype in the cnb1 background. Plasmids were recovered from the putative positive transformants and reintroduced into the original mutant strains. Eight cDNA clones (corresponding to one STO and seven STZ cDNA inserts, see below) retested as increasing salt tolerance of cna1 cna2 cells and ten cDNA clones (corresponding to four STO and six STZ cDNA inserts, see below) retested as increasing salt tolerance of cnb1 cells. Partial sequencing of the first seven positive clones (five from cna1 cna2 mutants and two from cnb cells) revealed that they corresponded to one of two sequences, STO or STZ. Hybridization of other positive clones with probes prepared from either STO or STZ cDNA inserts revealed that all new clones encoded either STO or STZ. Colonies representing 500,000 independent cDNA clones were screened in each cna1 cna2 cells and cnb mutants, and both STO and STZ were recovered in the two mutant backgrounds. Five STO cDNAs and 13 STZ cDNAs were identified of which at least 4 and 11 were independent isolates, respectively.

Figure 1B:
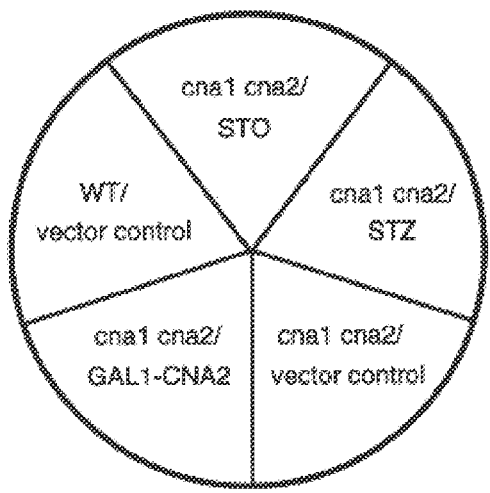
Figure 1B:
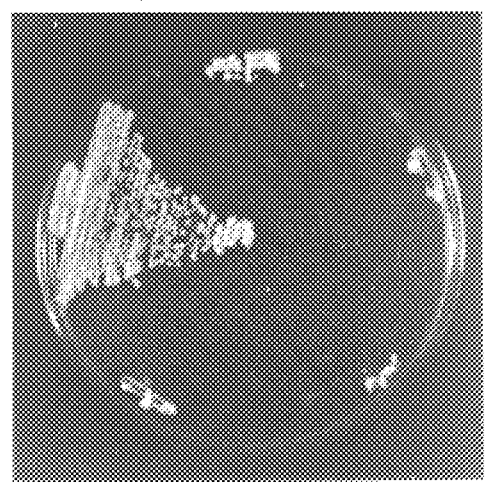
Figure 1C:
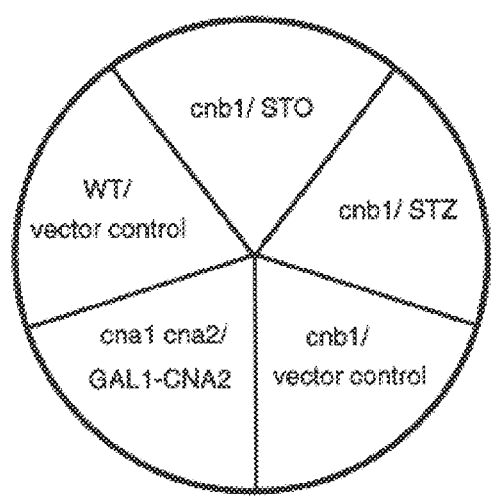
Figure 1C:
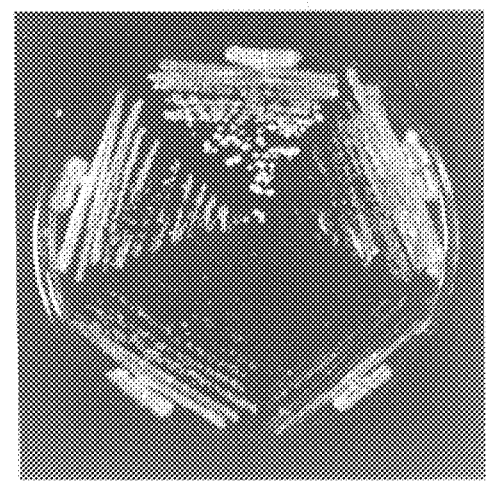

Calcineurin mutant strains harboring STO or STZ clones exhibited two distinct growth phenotypes on medium containing LiCl and galactose. Expression of STO lead to colonies that grew faster than either wild-type cells carrying the vector control or cna1 cna2 cells expressing CNA2 under the GALL promoter. In contrast, STZ-containing cells grew at approximately the same rate as these strains (FIG. 1A). These growth phenotypes were produced by the two clones in both mutant backgrounds and were accentuated at higher LiCl concentration (FIG. 1A and 1C and data not shown). Increased tolerance of cna1 cna2 mutants and cnb1 cells carrying the positive clones was abolished on medium containing LiCl and glucose (FIG. 1B and data not shown), showing that expression from the cDNA clones was galactose dependent. STO and STZ also conferred increased tolerance to NaCl in the presence of galactose to cna1 cna2 cells and to cnb1 mutants (data not shown). As was observed with LiCl, at elevated NaCl concentrations (e.g. 600 mM) expression of STO in the mutant backgrounds increased salt tolerance more than either STZ or GAL1-CNA2 (data not shown).

The open reading frame of the STO gene encodes a hydrophilic protein of 249 amino acids with an estimated molecular mass of 27.6 kDa and a calculated pI of 5.4. Analysis of the STO protein sequence reveals a region near the C-terminus in which a highly basic region is followed by a highly acidic region. The overall sequence of this protein is rich in glutamine residues. Comparison of the STO sequence with sequences in the GenBank database showed no significant similarity with proteins of known function but revealed similarity of this sequence to several randomly sequenced cDNAs (ESTs). STO was most similar to clone Atts 3129 from *Arabidopsis thaliana* and to rice clones 1479a, 15772a, 10131a. The Arabidopsis Atts 3129 sequence included significant differences compared to the STO cDNA so they are likely to derive from related but distinct genes.

STZ encodes a protein of 228 amino acids with a calculated molecular mass of 24.6 kDa and an estimated pI of 8.3 (SEQ. ID. Nos. 1 and 2). In contrast to S, the protein encoded by STZ is 37% to 68% identical in amino acid sequence to a family of petunia $Cys_2/His_2$-type zinc finger DNA-binding proteins associated with flowers (termed EPF) being most similar to EPF2-7 (68%) Takatsuji et al. (1994), supra. STZ also shows 47% amino acid identity with WZF1 Sakamoto et al. *Eur. J. Biochem.* 217:1049–1056 (1993), a wheat zinc finger DNA-binding protein which is highly expressed in the root apexes of wheat seedlings. Since WZF1 is distinctly different from members of the petunia EPF family it appears to be a separate member of this class of zinc finger proteins. STZ is more similar to the wheat member of this family of zinc finger proteins than it is to the most diverged member of the petunia sequences, indicating that this is a family whose divergence precedes the split between monocots and dicots.

STO and STZ cDNAs increase salt tolerance of wide-type yeast

The increased colony size on salt-containing medium of yeast calcineurin mutants expressing STO relative to an isogenic wild-type strain lead to an investigation as to whether expression of either STO or STZ confers a growth advantage on wild-type yeast in the presence of salt. FIG. 2 shows that wild-type strain producing STO or STZ grew faster in the presence of galactose and LiCl than the same strain harboring either a vector control or pGal1-CNA2. The growth advantage conferred by these clones was accentuated at higher salt concentration. No growth difference was observed on equivalent medium lacking salt. Similar results were observed when NaCl was used as the salt (data not shown).

In high salt liquid medium (YP galactose/raffinose containing 260 mM LiCl), wild-type strain containing plasmids that encode either STO or STZ grow at faster rates (4.7±0.2 h and 4.5±0.2 h doubling times, respectively; data not shown) than wild-type strain harboring a vector control plasmid (6.0±0.5 h doubling time). Doubling times were determined from four data sets for each strain. Similar differences were observed in media containing 0.7M NaCl.

Arabidopsis genomic DNA blot analysis

Genomic DNA blots were hybridized with the STO coding sequence probe at high stringency giving in a single band with an intensity similar to a single-copy control (data not shown) indicating the presence of a single STO gene in Arabidopsis. In contrast, when an equivalent blot was hybridized at high stringency with the STZ coding sequence probe, a number of weak hybridizing bands were observed in the various digests in addition to a strong hybridizing band, suggesting that the STZ gene is a member of a multigene family.

Expression of STO and STZ genes in Arabidopsis organs

To determine the expression pattern of the STO and STZ genes, blots were prepared with total RNA from roots, leaves, and flowers. The STO cDNA hybridized to a 1.1 kb transcript which is in good agreement with the size of the isolated STO cDNA inserts. The steady-state level of the STO mRNA was highest in leaves and was significantly lower in roots and flowers. The expression pattern of the STZ gene differs considerably from that of the STO gene. Two hybridizing bands of sizes corresponding to 0.9 kb and 0.7 kb were observed when a $^{32}$P-labeled cDNA fragment corresponding to the STZ gene was used. These results are consistent with the DNA blot data (see above) and the hypothesis that the STZ gene is part of a gene family. Both transcripts showed developmentally-regulated expression. The relative abundance of these mRNAs was coordinately regulated being present at significantly higher concentrations in roots than in leaves. Neither transcript was detectable in flowers. Identical blots were hybridized with Arabidopsis CyP (ROC1) probe to demonstrate equal loading in all lanes. When the above RNA blot hybridized with the STZ coding region probe was washed at higher stringency (0.3× SSPE, 0.1% SDS at 75° C.) the fast-migrating band was eluted (data not shown) indicating that the slow-migrating transcript (0.9 kb in length) corresponds to the STZ gene. This data is in good agreement with the insert sizes of the isolated STZ cDNA clones which were ~0.9 kb in length.
Expression of STO and STZ genes in NaCltreated Arabidopsis plants Since the Arabidopsis STO and STZ cDNAs conferred increased salt tolerance in yeast (see above), it was of interest to determine if the corresponding genes are induced in plants in the presence of elevated levels of salt. Blots were prepared with RNA isolated from NaCl-treated Arabidopsis plants and hybridized either with an STO or STZ cDNA probe. The steady-state level of the STO mRNA is essentially unchanged in plants treated with increasing NaCl concentrations (0, 80, 140 and 220 mM NaCl).

When a similar blot was hybridized with an STZ cDNA probe, two hybridizing bands were observed similar to the results above. The 0.9 kb transcript corresponded to the STZ gene based on a higher stringency was (see above). The steady state levels of the 0.9 kb transcript are similar in plants treated with 0, 80 or 140 mM NaCl but concentration of the transcript increases 2.5 fold when plants are treated with 220 mM NaCl. In contrast, the steady-state level of the 0.7 kb fragment is low in 0 mM NaCl-treated plants and increases approximately three-fold in the presence of 80 mM NaCl. At higher concentrations of NaCl the 0.7 kb mRNA levels are lower than at 80 mM NaCl being~2 fold higher relative to that at 0 mM NaCl. The differences in hybridization observed with the STZ cDNA probe at the various NaCl treatments cannot be explained by variations in gel loading of RNA from each treatment.

In conclusion, unlike the STO gene, the genes leading to the 0.7 and 0.9 kb transcripts appear to respond to NaCl in the medium and seem to respond differently from one another at a given salt concentration.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

SEQ. ID. Nos. 1 and 2

STZ clone: nucleotide sequence and deduced amino acid sequence

```
  1  GCAACCTTCAAACTAAAACTCGAGAGACAAGAAATCCTCAGAATCTTTAACTTAATGGCG    60
                                                              M  A

61  CTCGAGGCTCTTACATCACCAAGATTAGCTTCTCCGATTCCTCCTTTGTTCGAAGATTCT   120
      L  E  A  L  T  S  P  R  L  A  S  P  I  P  P  L  F  E  D  S

121  TCAGTCTTCCATGGAGTCGAGCACTGGACAAAGGGTAAGCGATCTAAGAGATCAAGATCC   180
      S  V  F  H  G  V  E  H  W  T  K  G  K  R  S  K  R  S  R  S

181  GATTTCCACCACCAAAACCTCACTGAGGAAGAGTATCTAGCTTTTTGCCTCATGCTTCTC   240
      D  F  H  H  Q  N  L  T  E  E  E  Y  L  A  F  C  L  M  L  L

241  GCTCGCGACAACCGTCAGCCTCCTCCTCCTCCGGCGGTGGAGAAGTTGAGCTACAAGTGT   300
      A  R  D  N  R  Q  P  P  P  P  P  A  V  E  K  L  S  Y  K  C

301  AGCGTCTGCgACAAGACGTTCTCTTCTTACCaAGCTCTCGGTGGTCACAAGGCAAGCCAC   360
      S  V  C  D  K  T  F  S  S  Y  Q  A  L  G  G  H  K  A  S  H

361  CGTAAGAACTTATCACAGACTCTCTCCGGCGGAGGAGATGATCATTCAACCTCGTCGGCG   420
      R  K  N  L  S  Q  T  L  S  G  G  D  D  H  S  T  S  S  A

421  ACAACCACATCCGCCGTGACTACTGGAAGTGGGAAATCACACGTTTGCACCATCTGTAAC   480
      T  T  T  S  A  V  T  T  G  S  G  K  S  H  V  C  T  I  C  N

481  AAGTCTTTTCCTTCCGGTCAAGCTCTCGGCGGACACAAGCGGTGCCACTACGAAGGAAAC   540
      K  S  F  P  S  G  Q  A  L  G  G  H  K  R  C  H  Y  E  G  N

541  AACAACATCAACACTAGTAGCGTGTCCAACTCCGAAGGTgCGGGGTCCACTAGCCACGTT   600
      N  N  I  N  T  S  S  V  S  N  S  E  G  A  G  S  T  S  H  V

601  AGCAGTAGCCACCGTGGGTTTGACCTCAACATCCCTCCGATCCCTGAATTCTCGATGGTC   660
      S  S  S  H  R  G  F  D  L  N  I  P  P  I  P  E  F  S  M  V

661  AACGGAGACGACGAAGTCATGAGCCCTATGCCGGCGAAGAAGCCTCGGTTTGACTTTCCG   720
      N  G  D  D  E  V  M  S  P  M  P  A  K  K  P  R  F  D  F  P

721  GTCAAACTTCAACTTTAAGGAAATTTACTTAGACGATAAGATTTCGTTTGTATACTGTTG   780
      V  K  L  Q  L  *
```

-continued

STZ clone: nucleotide sequence and deduced amino acid sequence

```
781  AGAGTTGTGTAGGAATTTGTTGACTGTACATACCAAATTGGACTTTGACTGATTCCAATT  840

841  CTTCTTGTTCTTTCATTTTAAAAATTATTAAACCGATTCTTTACCACAAAAAAAAAAAAA  900

901  AAAAAAAAAAAAAAAAAAAAAAAAAAAAAAAAAAAAAAAA  940
```

SEQ. ID. Nos. 3 and 4

STO clone: nucleotide sequence and deduced amino acid sequence

```
  1  TCTGAACCTACGCTTCTGCTAAGCTATTCTAAGAGAAGCCAGACTAGCAATAAACCCTTC   60

61  ATTTTAAGCATTCTGTTTCCTTCTTGAGAAACCTAGATATTTTGGTTTCTTGTATCCGGT  120

121  GATGAAGATACAGTGTGATGTGTGTGAGAAAGCTCCGGCGACGGTGATTTGTTGCGCCGA  180
      M  K  I  Q  C  D  V  C  E  K  A  P  A  T  V  I  C  C  A  D
181  CGAAGCTGCTCTCTGTCCTCAATGCGACATCGAGATTCACGCCGCTAACAAACTCGCTAG  240
      E  A  A  L  C  P  Q  C  D  I  E  I  H  A  A  N  K  L  A  S
241  CAAGCACCAACGTCTTCATCTTAATTCCCTCTCCACCAAATTCCCTCGTTGCGATATCTG  300
      K  H  Q  R  L  H  L  N  S  L  S  T  K  F  P  R  C  D  I  C
301  CCAAGAGAAGGCAGCTTTCATTTTCTGTGTAGAGGATAGAGCTCTGCTTTGCAGGGACTG  360
      Q  E  K  A  A  F  I  F  C  V  E  D  R  A  L  L  C  R  D  C
361  CGATGAATCCATCCACGTGGCTAATTCTCGATCTGCTAATCACCAGAGGTTCTTAGCCAC  420
      D  E  S  I  H  V  A  N  S  R  S  A  N  H  Q  R  F  L  A  T
421  TGGGATCAAAGTAGCTCTGACCTCAACTATATGTAGTAAAGAAATTGAGAAGAATCAACC  480
      G  I  K  V  A  L  T  S  T  I  C  S  K  E  I  E  K  N  Q  P
481  TGAGCCTTCCAACAACCAACAGAAGGCTAATCAGATTCCTGCTAAATCCACAAGCCAGCA  540
      E  P  S  N  N  Q  Q  K  A  N  Q  I  P  A  K  S  T  S  Q  Q
541  GCAACAACAACCTTCTTCTGCTACTCCACTTCCCTGGGCTGTTGACGATTTCTTTCACTT  600
      Q  Q  Q  P  S  S  A  T  P  L  P  W  A  V  D  D  F  F  H  F
601  CTCTGATATTGAATCCACCGACAAGAAAGGACAGCTTGATCTTGGGGCAGGGGAGTTGGA  660
      S  D  I  E  S  T  D  K  K  G  Q  L  D  L  G  A  G  E  L  D
661  TTGGTTTTCAGACATGGGATTCTTCGGTGATCAGATTAATGACAAGGCTCTTCCTGCAGC  720
      W  F  S  D  M  G  F  F  G  D  Q  I  N  D  K  A  L  P  A  A
721  TGAAGTTCCTGAGCTTTCTGTTTCGCATTTAGGTCATGTTCATTCATACAAACCTATGAA  780
      E  V  P  E  L  S  V  S  H  L  G  H  V  H  S  Y  K  P  M  K
781  GTCAAATGTTTCACACAAGAAGCCGAGGTTTGAGACCAGATATGATGATGATGATGAGGA  840
      S  N  V  S  H  K  K  P  R  F  E  T  R  Y  D  D  D  D  E  E
841  ACACTTCATTGTCCCTGATCTTGGCTAAAAAGCTATATGTAATCTATGTGTAGACATTCT  900
      H  F  I  V  P  D  L  G  *
901  TCAATGTAAAAGAACAAACAAGAAACCTATCTGCATGTGTGGAGTTAATGTCATATACAT  960

961  TTTAGTTTTGTCTTAAGTTGTGTAAGATATGTTGAGAGCTTATAACAAATGTCTGTGTTT 1020

1021 GAGTTAAAAAAAA  1033
```

---

What is claimed is:

1. An isolated nucleic acid construct comprising an STO polynucleotide sequence which comprises at least about 200 nucleotides and hybridizes to SEQ. ID. No. 3 under hybridization conditions which include washing with a solution having a salt concentration of about 0.02 molar at pH 7 and at about 60° C.

2. The nucleic acid construct of claim 1, wherein the STO polynucleotide sequence encodes an STO polypeptide as shown in SEQ. ID. No. 4.

3. The nucleic acid construct of claim 1, wherein the polynucleotide sequence is a full length STO gene.

4. The nucleic acid construct of claim 1, wherein the STO polynucleotide sequence is as shown in SEQ. ID. No. 3.

5. The nucleic acid construct of claim 1, further comprising a promoter operably linked to the STO polynucleotide sequence.

6. The nucleic acid construct of claim 5, wherein the promoter is a tissue-specific promoter.

7. The nucleic acid construct of claim 5, wherein the promoter is a constitutive promoter.

8. A transgenic plant comprising a recombinant expression cassette comprising a plant promoter operably linked to an STO polynucleotide sequence which comprises at least about 200 nucleotides and hybridizes to SEQ. ID. No. 3 under hybridization conditions which include washing with a solution having a salt concentration of about 0.02 molar at pH 7 and at about 60° C.

9. The transgenic plant of claim 8, wherein the plant promoter is a heterologous promoter.

10. The transgenic plant of claim 8, wherein the STO polynucleotide sequence encodes an STO polypeptide as shown in SEQ. ID. No. 4.

11. The transgenic plant of claim 8, wherein the polynucleotide sequence is as shown in SEQ. ID. No. 3.

12. An isolated nucleic acid construct comprising an STO polynucleotide sequence that encodes an STO polypeptide as shown in SEQ. ID. No. 4.

13. A transgenic plant comprising a recombinant expression cassette comprising a plant promoter operably linked to an STO polynucleotide sequence that encodes an STO polypeptide as shown in SEQ. ID. No. 4.

* * * * *